Figure 1J:
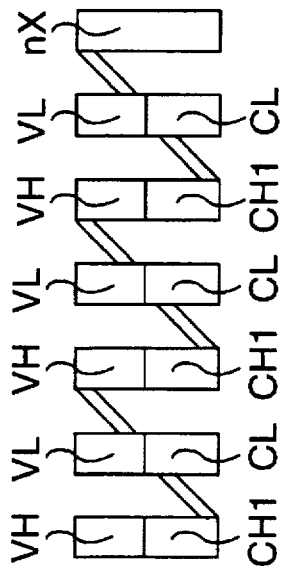
Figure 1I:
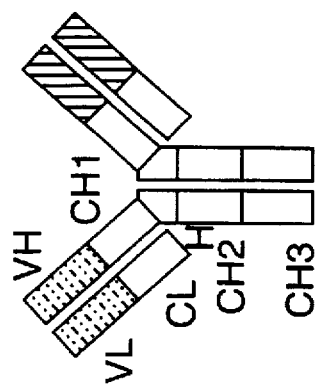

US005686583A

United States Patent [19]
Bosslet et al.

[11] Patent Number: 5,686,583
[45] Date of Patent: Nov. 11, 1997

[54] SPECIFIC ANTIBODIES AGAINST ACTIVATED PLATELETS, THE PREPARATION THEREOF AND THE USE THEREOF IN DIAGNOSIS AND THERAPY

[75] Inventors: Klaus Bosslet, Marburg; Gerhard Seemann, Marburg-Elnhausen; Beate Kehrel, Münster, all of Germany

[73] Assignee: Behringwerke Aktiengesellschaft, Marburg, Germany

[21] Appl. No.: 467,393

[22] Filed: Jun. 6, 1995

Related U.S. Application Data

[63] Continuation of Ser. No. 268,566, Jul. 6, 1994, abandoned, which is a continuation of Ser. No. 13,383, Feb. 4, 1993, abandoned.

[30] Foreign Application Priority Data

Feb. 7, 1992 [DE] Germany .................. 42 03 545.7

[51] Int. Cl.$^6$ .................. A61K 39/395; C07K 16/28; C12N 5/12
[52] U.S. Cl. .................. 530/387.3; 530/389.7; 530/391.3; 435/328; 435/320.1; 435/344; 424/9.1; 536/23.53
[58] Field of Search ............... 530/387.3, 389.7, 530/391.3; 435/240.27; 424/1.49; 536/23.53

[56] References Cited

U.S. PATENT DOCUMENTS 4,610,960  9/1986  Mosher.

FOREIGN PATENT DOCUMENTS

| 0 387 380 A1 | 9/1990 | European Pat. Off. . |
| A0443404A1 | 8/1991 | European Pat. Off. . |
| A0514721A1 | 11/1992 | European Pat. Off. . |
| WO 91/06858 | 5/1991 | WIPO . |
| WO 91/10424 | 7/1991 | WIPO . |
| WO 92/17499 | 10/1992 | WIPO . |

OTHER PUBLICATIONS

D. Collen, The Lancet, 1993, 342:34.
Harlow et al., 1988, pp. 285–287.
Morrison et al., Hospital Practice, 1989, pp. 65–80.
A Thrombin–Sensitive Protein of Human Platelet Membranes, Baenziger et al. Proc. Nat. Acad. Sci., 68:240–243 (1971).
Immunohistochemical Localization of Membrane and α–Granule Proteins in Human Megakaryocytes: Application to Plastic–Embedded Bone Marrow Biopsy Specimens, Beckstead et al., Blood, 67(2):285–293 (1986).
Immunohistochemical Localization and Molecular Characteristics of Three Monoclonal Antibody–Defined Epitopes Detectable on Carcinoembryonic Antigen (CEA), Bosslet et al., Int. J. Cancer, 36:75–84 (1985).
Immunoenzymatic Labeling of Monoclonal Antibodies Using Immune Complexes of Alkaline Phosphatase and Monoclonal Anti–Alkaline Phosphatase (APAAP Complexes), Cordell et al., J. Histochem. (Cytochem., 32(2):219–229 (1984).

Effects of Anti–Thrombospondin Monoclonal Antibodies on The Agglutination of Erythrocytes and Fixed, Activated by Purified Thrombospondin, Dixit et al., Biochemistry, 24:4270–4275 (1985).
Isolation and Characterization of a Heparin–Binding Domain From The Amino Terminus of Platelet Thrombospondin, Dixit et al., J. Biol. Chem., 259(16):10100–10105 (1984).
Immunochemical Identification of a Thrombospondin–Like Structure In An Arterial Microfibrillar Extract, Fauvel–Lafeve et al., Thromb. Research, 50:305–316 (1988).
Isolation and Properties of a Thrombin–Sensitive Protein from Human Blood Platelets, Ganguly, J. Biol. Chem., 246(13):4268–4290 (1971).
Humanization of Monoclonal Antibodies, Güssow et al., Methods in Enzymology, 203:99–121 (1991).
Antigenic Sites in Carcinoembryonic Antigen, Hammarstrom et al., Cancer Research, 49:4852–4858 (1989).
Antibody–Targeted Thrombolytic Agents, Haber et al., Japanese Circulation Journal, 54:345–353 (1989).
Multimerin: A Series of Large Disulfide–Linked Multimeric Proteins Within Platelets, Hayward et al., Blood, 77 (12):2555–2560 (1991).
Evolution of Human Immunoglobulin k J Region Genes, Hieter et al., Journal of Biological Chemistry, 257(3):1516–1522 (1982).
Establishment of Mammalian Cell Lines Containing Multiple Nonsense Mutations and Functional Suppressor tRNA Genes, Hudziak et al., Cell, 31:137–146 (1982).
Cultured Human Fibroblasts Synthesize and Secrete Thrombospondin and Incorporate it into Extracellular Matrix, Jaffe et al., Proc. Natl. Acad. Sci. USA, 80:998–1002 (1983).
Glucocorticoids Regulate Expression of Dihydrofolate Reductase cDNA in Mouse Mammary Tumour Virus Chimaeric Plasmids, Lee et al., Nature, 294:228–232 (1981).
Use of Radiolabelled Monoclonal Anti–CEA Antibodies for the Detection of Human Carcinomas by External Photoscanning and Tomoscintigraphy, Mach et al., Immunology Today, 2:239–249 (1981).
Thrombospondin is Present in Articular Cartilage and is Synthesized by Articular Chondocytes, Miller et al., Biochem. Biophys. Res. Commun., 153(2):708–714 (1988).
Regulation of Thrombospondin Secretion by Cells in Culture, Mumby et al., J. Cell. Physiol., 120:280–288 (1984).
High Resolution Two–Dimensional Electrophoresis of Proteins, O'Farrell, J. Biol. Chem., 250(10):4007–4021 (1975).

(List continued on next page.)

*Primary Examiner*—Frank C. Eisenschenk
*Attorney, Agent, or Firm*—Finnegan, Henderson, Farabow, Garrett & Dunner, L.L.P.

[57] ABSTRACT

The invention relates to monoclonal antibodies and parts thereof which bind preferentially to active human platelets, to the nucleotide sequence and amino-acid sequence of the heavy and light chain of MAb BW 2128 and to an antigen associated with thrombospondin.

16 Claims, 16 Drawing Sheets

OTHER PUBLICATIONS

Cloning Immunoglobulin Variable Domains for Expression By the Polymerase Chain Reaction, Orlandi et al., Proc. Natl. Acad. Sci. USA, 86:3833–3837 (1989).

A New Medium Improves Sampling for Determination of Platelet Factor 4 in Human Plasma, Osei–Bonsu et al., Wiener Klin. Wschr. 99:595–600 (1987).

Evaluation of the In Vitro and Ex Vivo Blood Compatibility of Primary Reference Materials, Pelzer et al., Journal of Biomedical Material Res. 20:1401–1409 (1986).

Thrombospondin Is An Osteoblast–Derived Component of Mineralized Extracellular Matrix, Robey et al., J. Cell Biol., 108:719–727 (1989).

A Novel Approach to Tc–99m–Labeled Monoclonal Antibodies, Schwarz et al., J. Nucl. Med., 28 (4):721 (1987).

Granular Pneumocytes in Primary Culture Secrete Several Major Components of the Extracellular Matrix, Sage et al., Biochemistry, 22:2148–2155 (1983).

DNA Sequencing With Chain–Terminating Inhibitors, Sanger et al., Proc. Natl. Acad. Sci. USA, 74(12):5463–5467 (1977).

Expression of Biologically Active Human Antithrombin III in Chinese Hamster Ovary Cells, Zettlmeissl et al., Bio/Technology, 5:720–725 (1987).

Design and Synthesis of a Mimetic From an Antibody Complementarity Determining Region, Saragovi et al., Science, 253:792–795 (1991).

Light Microscopic Immunolocation of Thrombospondin in Human Tissues, Wight et al., Journal of Histochem. and Cytochem., 33(4):295–302 (1985).

Electrophoretic Transfer of Proteins From Polyacrylamide Gels to Nitrocellulose Sheets: Procedure And Some Applications, Towbin et al., Proc. Natl. Acad. Sci. USA, 76(9):4350–4354 (1979).

Isolation of Overproducing Recombinant Mammalian Cell Lines By a Fast And Simple Selection Procedure, Wirth et al., Gene, 73:419–426 (1988).

Efficient Expression System for Human Antithrombin III in Baby Hamster Kidney Cells, Zettlmeissl et al., Behring Institute Mitteilungen 82:26–34 (1988).

K. Bosslet, et al., "Quantitative considerations supporting the irrelevance of circulating serum CEA for the immunoscintigraphic visualization of CEA expressing carcinomas," *European Journal of Nuclear Medicine* (1988) 14:523–528.

Gert Riethmüller, et al., "Randomized trial of monoclonal antibody for adjuvant therapy of resected Dukes' C colorectal carcinoma," *The Lancet*, vol. 343 (May 14, 1994), pp. 1177–1183.

Maria I Colnaghi, et al., "Evolution of the therapeutic use of new monoclonal antibodies," *Current Opinion in Oncology*, (1993), 5:1035–1042.

Asch et al., "Cellular Attachment to Thrombospondin, Cooperative Interactions Between Receptor Systems," J. Biol. Chem., 266(3):1740–1745 (1991).

Winter et al., "Man–made Antibodies," Nature, 349:293–299 (1991).

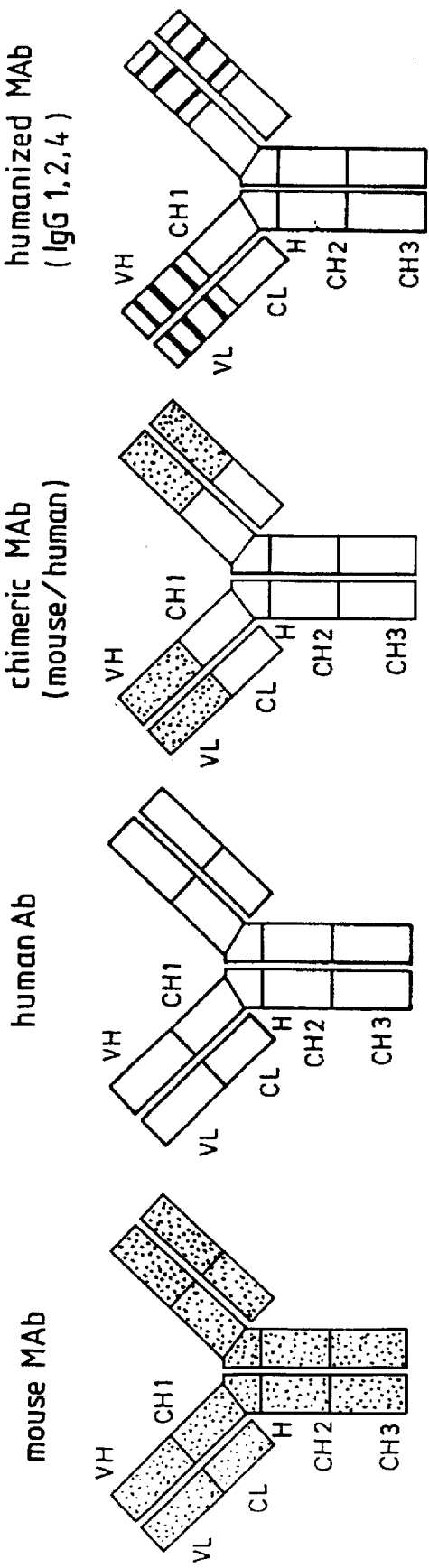
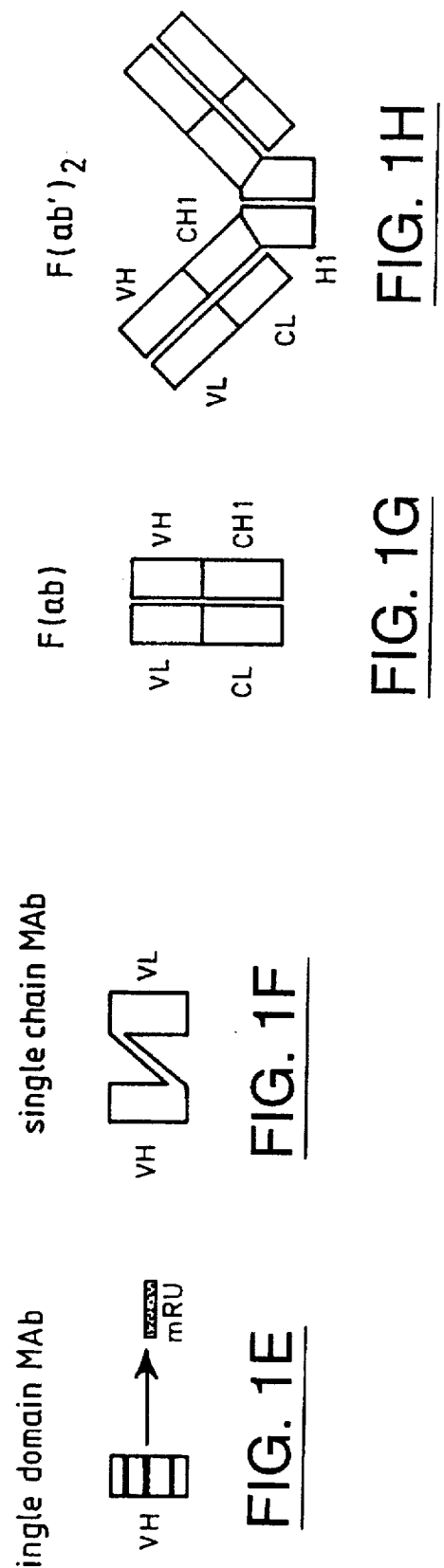

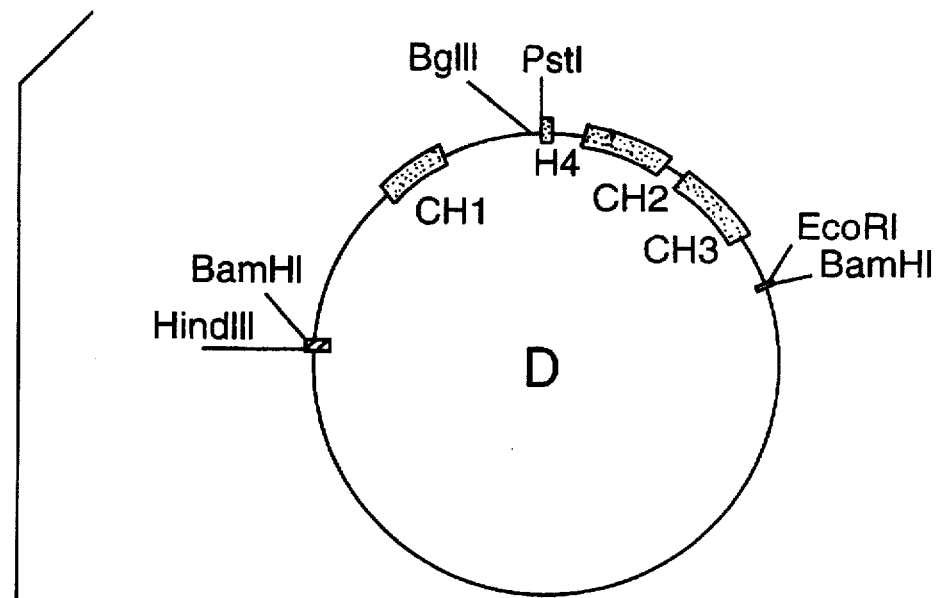
FIG. 6
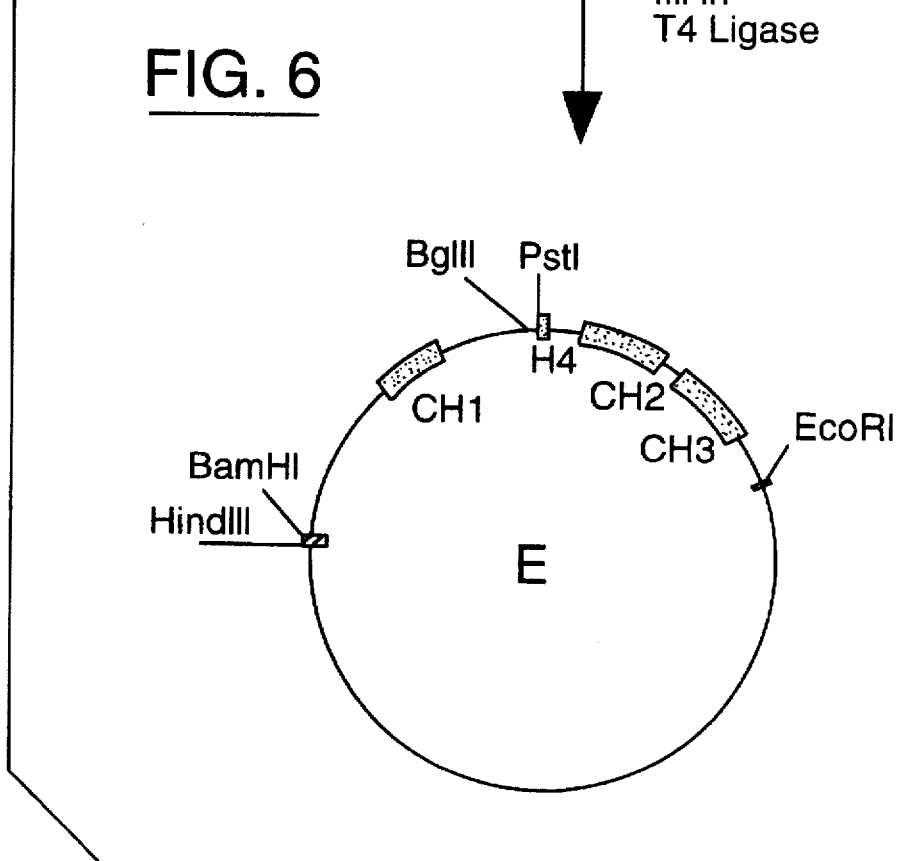

pR11H140

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:

(A) LENGTH: 357 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

| | | | | | |
|---|---|---|---|---|---|
| CTGCAGCAGT | CTGGGGCTGA | ACTGGTGAAG | CCTGGGGCTT | CAGTGACCCT | GTCCTGTAAG | 60 |
| GCTTCTGGCT | ACACCTTCAC | CAGCTACTGG | ATGCACTGGG | TGAAGCAGAG | GCCTGGACAA | 120 |
| GGCCTTGAGT | GGATTGGAGA | GATTAATCCT | AGCAACGGTC | GTACTAACTA | CAATGAGAAG | 180 |
| TTCAAGAGCA | AGGCCACACT | GACTGTAGAC | AAATCCTCCA | GCACAGCCTA | CATGCACCTC | 240 |
| AGCAGCCTGA | CATCTGATGA | CTCTGCGGTC | TATTACTGTG | CAAGAGGGGC | TGGGGCGGGA | 300 |
| GGCTACTGGG | GCCAAGGGAC | CACGGTCACC | GTCTCCTCAG | GTGAGTCCTT | ACAACCT | 357 |

(2) INFORMATION FOR SEQ ID NO:2:

(i) SEQUENCE CHARACTERISTICS:
(A) LENGTH: 119 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

```
Leu Gln Gln Ser Gly Ala Glu Leu Val Lys Pro Gly Ala Ser Val Thr
  1               5                  10                  15
Leu Ser Cys Lys Ala Ser Gly Tyr Thr Phe Thr Ser Tyr Trp Met His
                 20                  25                  30
Trp Val Lys Gln Arg Pro Gly Gln Gly Leu Glu Trp Ile Gly Glu Ile
             35                  40                  45
Asn Pro Ser Asn Gly Arg Thr Asn Tyr Asn Glu Lys Phe Lys Ser Lys
         50                  55                  60
Ala Thr Leu Thr Val Asp Lys Ser Ser Ser Thr Ala Tyr Met His Leu
 65                  70                  75                  80
Ser Ser Leu Thr Ser Asp Asp Ser Ala Val Tyr Tyr Cys Ala Arg Gly
                 85                  90                  95
Ala Gly Ala Gly Gly Tyr Trp Gly Gln Gly Thr Thr Val Thr Val Ser
            100                 105                 110
Ser Gly Glu Ser Leu Gln Pro
            115
```

(2) INFORMATION FOR SEQ ID NO:3:

(i) SEQUENCE CHARACTERISTICS:
(A) LENGTH: 309 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| CAGCTGACCC | AGTCTCCAGC | AATCATGTCT | GCATCTCCAG | GGGAGAAGGT | CACCATGACC | 60 |
| TGCAGTGCCA | GCTCAAGTGT | AACTTACATG | CACTGGTGCC | AGCAGAAGTC | AGGCACCTCC | 120 |
| CCCAAAAGAT | GGATTTATGA | CACATCCAAA | CTGGCTTCTG | GAGTCCCTGC | TCGCTTCAGT | 180 |
| GGCAGTGGGT | CTGGGACCTC | TTACTCTCTC | ACAATCAGCA | GCATGGAGGC | TGAAGATGCT | 240 |
| GCCACCTATT | ACTGCCAGCA | GTGGAATAGT | AACCCGCTCA | CGTTCGGTGC | TGGGACCAAG | 300 |

CTGGAGATC 309

(2) INFORMATION FOR SEQ ID NO:4:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Gln Leu Thr Gln Ser Pro Ala Ile Met Ser Ala Ser Pro Gly Glu Lys
  1           5                  10                  15

Val Thr Met Thr Cys Ser Ala Ser Ser Ser Val Thr Tyr Met His Trp
             20                  25                  30

Cys Gln Gln Lys Ser Gly Thr Ser Pro Lys Arg Trp Ile Tyr Asp Thr
         35                  40                  45

Ser Lys Leu Ala Ser Gly Val Pro Ala Arg Phe Ser Gly Ser Gly Ser
     50                  55                  60

Gly Thr Ser Tyr Ser Leu Thr Ile Ser Ser Met Glu Ala Glu Asp Ala
 65                  70                  75                  80

Ala Thr Tyr Tyr Cys Gln Gln Trp Asn Ser Asn Pro Leu Thr Phe Gly
                 85                  90                  95

Ala Gly Thr Lys Leu Glu Ile
             100
```

SPECIFIC ANTIBODIES AGAINST ACTIVATED PLATELETS, THE PREPARATION THEREOF AND THE USE THEREOF IN DIAGNOSIS AND THERAPY

This application is a continuation of application Ser. No. 08/268,566, filed Jul. 6, 1994, which is a continuation of application Ser. No. 08/013,383 filed Feb. 4, 1993, both abandoned.

Hybridoma technology makes it possible to prepare selective monoclonal antibodies (MAbs) against any desired epitopes on defined or undefined antigens. Immunogens which can be used for this are highly purified, defined antigens or else antigen mixtures, cells or tissue, and for finding highly selective MAbs it is also necessary to find a suitable immunogen. It has now been possible using this technology to develop MAbs which are able after i.v. injection to bind, for example, to tumors, inflammatory processes and vascular occlusions in the human body. This preferential binding of MAbs to the corresponding target structures (tumor, inflammatory process, vascular occlusion) is already used in nuclear medical diagnosis. The specific nuclear medical discipline which deals with the injection of radioactively labeled MAbs for detecting target structures is immunoscintigraphy (Mach, J. P., Buchegger, F., Forni, M., Ritschard, J., Berche, C., Lumbraso, J. -O., Schreyer, M., Girardet, C., Accolla, R. C., Carrel, S. (1981). Immunology today 2:239–249). Currently, no MAbs which selectively bind to platelets and essentially not to other normal human tissue are available for this. Even the MAbs which are directed against α-granule proteins of platelets and which indeed bind preferentially to activated platelets nevertheless show distinct binding to epitopes on other tissues. Thus, for example, MAbs which are directed against thrombospondin (TSP), an α-granule protein (Baenziger, N. L., Brodie, G. N., Majerus, P. W. (1971). Proc. Nat. Acad. Sci. USA 68: 240–243; Ganguly, P. (1971). J. Biol. Chem. 246:4286–4290) react with epitopes in the glandular epithelium of the skin and lungs, the connections between dermis and epidermis (Wight, T. N., Raugi, G. J., Mumby, S. M., Bornstein, D. (1985). J. Histochem. Cytochem. 33:295–302), the cartilage (Miller, R. R., McDevitt, C. A. (1988). Biochem. Biophys. Res. Commun. 153:708–714), decalcified bone (Robey, P. G., Young, M. F., Fisher, L. W., McClain, T. D. (1989). J. Cell. Biol. 108:719–727), umbilical arteries (Fauvel-Lafeve, F., Legrand, Y. J. (1988). Thromb. Res. 50:305–316), type II pneumocytes (Sage, H., Farin, F. M., Striker, G. E., Fisher, A. B. (1983). Biochemistry 22:2148–2155), megacaryocytes (Beckstead, J. H., Stenberg, P. E., McEver, R. P., Shuman, M. A., Bainton, D. F. (1986). Blood 67:285–293) and proliferating endothelial cells, smooth muscle and fibroblasts (Mumby, S. M., Abbott-Brown, D., Raugi, G. J., Bornstein, P. (1984). J. Cell. Physiol. 120:280–288; Jaffe, E. A., Ruggiero, J. T., Leung, L. K., Doyle, M. J., McKeown-Lango, P. J., Mosher, D. F. (1983). Proc. Nat. Acad. Sci. USA 80:998–1002). Owing to the cross-reactivities with the normal tissues which have just been mentioned, false-positive signals are generally to be observed when it is attempted to detect vascular occlusions in vivo with known anti-TSP MAbs.

When preparing αTSP MAbs by the method of Jaffe et al. (supra), we have surprisingly found a specific MAb against activated platelets (MAb BW 2128) which, in the Western blot described by Towbin T. & Gordon J. (1979) Proc. Natl. Acad. Sci. USA 76, 4350–434, reacts neither with known α-granule proteins such as TSP, v. Willebrand factor or gP 140 nor with the abovementioned cells or tissues. The MAb immunoprecipitates an antigen which is associated with TSP, has an isoelectric point which is indistinguishable from TSP within the limits of experimental error but has under reducing conditions a distinctly smaller molecular weight than TSP of about 160 kDa.

The limits of experimental error in the determination of the isoelectric point are about ±10–15%, in particular about ±5–10%.

The invention therefore relates to:

A hybridoma 2128 (DSM ACC2024).

A monoclonal antibody which is derived (BW 2128) from the hybridoma 2128 (DSM ACC2024).

Monoclonal antibodies or parts thereof which bind to an epitope which is recognized by a monoclonal antibody of the hybridoma 2128.

Monoclonal antibodies or parts thereof which preferentially bind to activated human platelets and contain an amino-acid sequence as shown in Tab. 1a (SEQ ID NO: 2) and/or Tab. 1b (SEQ ID NO: 4) or any allelic variant or mutant thereof which has the biological property of binding to an epitope which is recognized by the monoclonal antibody of the hybridoma 2128.

Preferential binding means for the purpose of the invention that 3–1000 times and, in particular, 10–100 times more epitopes which are recognized by BW 2128 are to be found on activated platelets than on non-activated platelets.

The invention furthermore relates to monoclonal antibodies or parts thereof which are chimeric, humanized, bi- or oligospecific in nature. Especially included therein are an mru fragment, a single domain fragment, a single chain fragment, an F(ab) fragment or an F(ab')$_2$ fragment with one or more hinge regions, as depicted, for example, in FIGS. 1A–1H and FIGS. 1I–1K.

Humanized antibodies are particularly preferred examples thereof.

An mru (minimal recognition unit) is a polypeptide which is derived from a CDR (complementarity determining region) and which has the property of binding to the epitope recognized by the specific MAb.

The invention also relates to mimetics which bind to an epitope which is recognized by the monoclonal antibody BW 2128. Small organic chemical compounds with high potential for binding to the epitope defined by BW 2128 are suitable as mimetics.

The invention generally relates to polypeptides containing an amino-acid sequence as shown in Tab. 1a (SEQ ID NO: 2) and/or Tab. 1b (SEQ ID NO: 4) or any allelic variant or mutant thereof which has the biological property of binding to an epitope which is recognized by the monoclonal antibody BW 2128.

It is particularly advantageous for the monoclonal antibodies according to the invention, or parts thereof, or the mimetics according to the invention to be used as fusion proteins which contain an immunoglobulin portion according to the invention and a part which does not belong to the immunoglobulin family.

The protein not belonging to the immunoglobulin family is to be, in particular, a fibrinolytic protein or parts thereof, for example the fibrinolytic protein streptokinase, urokinase, tPA, tPA mutants or parts thereof.

Also included therein are vectors, especially the expression vectors L1 and L2 and suitable host cells, especially COS, CHO or BHK cells, preferably BHK cells.

The invention furthermore relates to polynucleotides which contain one or more nucleic acid sequences which code for a polypeptide which has the biological property of binding to an epitope which is recognized by the monoclonal antibody BW 2128. These include, in particular, nucleic acids as shown in Tab. Ia (SEQ ID NO: 2) and Ib, (SEQ ID NO: 4), the degenerate codons thereof and nucleic acids which hybridize with the nucleic acids as shown in Tab. Ia (SEQ ID NO: 2) and Ib (SEQ ID NO: 4) under generally known hybridization conditions. Preferred hybridization conditions are stringent conditions as explained in Sambrook, J., Fritsch, E. F., Maniatis, T. (1982), Molecular cloning: a laboratory manual, Cold Spring Harbor Laboratory, Sambrook, J., Fritsch, E. F., Maniatis, T. (1989), Second Edition, Molecular cloning: A Laboratory Manual, Cold Spring Harbor Laboratory Press.

The invention furthermore relates to a process for the preparation of a polypeptide according to the invention, wherein a prokaryotic or eukaryotic host cell is transformed or transfected with a polynucleotide according to the invention so that the host cell expresses the said polypeptide. The polypeptide can then be isolated from the culture by methods known to the person skilled in the art.

The invention furthermore relates to an antigen or immunologically reactive parts thereof which is specifically recognized by one of the antibodies according to the invention, in particular by MAb BW 2128.

The general methods of genetic manipulation are known to the person skilled in the art and can be taken, unless otherwise, for example from Molecular Cloning: A Laboratory Manual; Sambrook et al. (supra).

The polypeptides according to the invention can, however, also be prepared chemically by methods of peptide synthesis which are known to the person skilled in the art.

By polypeptide is meant for the purpose of the invention proteins or amino-acid sequences including their spatial configuration and post-translational modifications, such as glycosylation or phosphorylation.

The Figures are briefly described hereinafter:

FIGS. 1A–1H: Diagrammatic representation of antibodies, recombinant antibodies, antibody fragments and antibody conjugates linked by genetic manipulation.

Figure 1K:
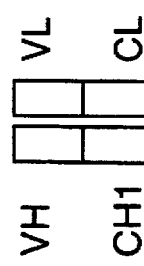
Figure 2:
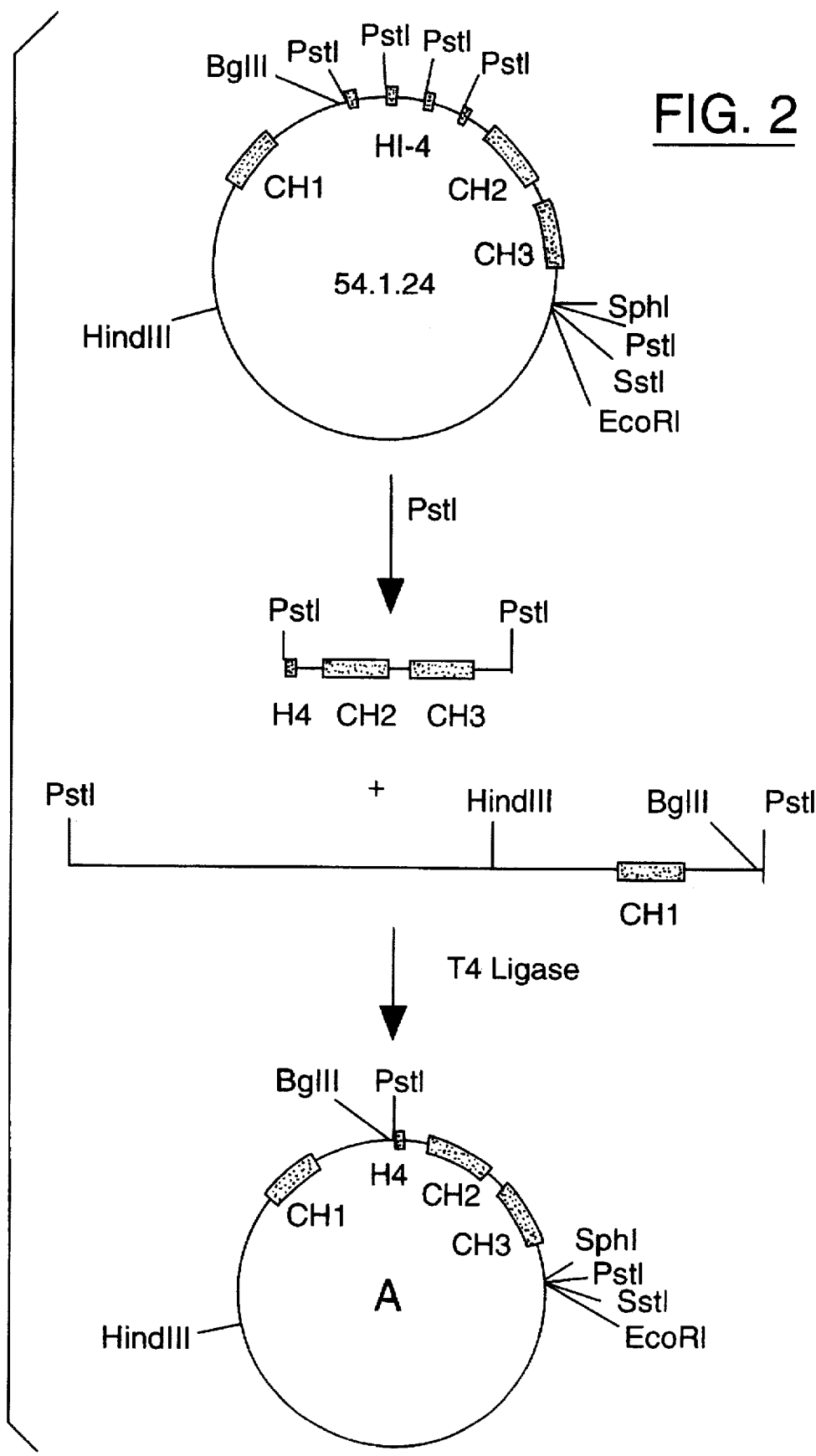

FIGS. 1K–1K: Diagrammatic representation of antibody conjugates. The various antigen-binding specificities of the bispecific antibody are made clear by different shading of the V regions. In the case of the oligospecific macromolecule, in each case the $C_{H1}$ domains are linked via polypspride linkers to the next $V_H$ domains, while the light chains are associated. The enzyme in the antibody/enzyme conjugate is depicted by dots.

FIGS. 2–15 are graphical representations of plasmid constructs for the recombinant production of antibodies.

The invention is particularly suitable in the in vivo detection and therapy of diseases in which activated platelets are involved, such as, for example, thromboses, specifically in cases of myocardial infarct or stroke, in thrombolytic therapy, deep vein thromboses, pulmonary embolisms, vascular injuries, atherosclerotic plaques, pyogenic infections and intestinal ischemias.

The MAb BW 2128 can be prepared as follows:

Human TSP was isolated from activated human platelets as described by Dixit, V. M., Hayerstick, D. M., O'Rourke, K. M., Hennessy, S. W., Grant, G. A., Santoro, S. A., Frazier, W. A. (1985), Biochemistry 24:4270–4275 and used for immunizing Balb/c mice by a known regimen (Bosslet, K., Lüben, G., Schwarz, A., Hundt, E., Harthus, H. P., Seiler, F. R., Muhrer, C., Klöppel, G., Kayser, K., Sedlacek, H. H. (1985), Int. J. Cancer 36:75–84). (This TSP preparation may be contaminated with other platelet proteins.) The supernatants from the resulting hybridomas were investigated for specificity on cryopreserved human tissues using the indirect APAAP technique (Cordell, J. L., Falini, B., Erber, W. N. et al. (1984), J. Histochem. Cytochem. 32:219). In general, the supernatants reacted with activated human platelets, with duct epithelium of the liver, vessels in the kidney, lung epithelium, spleen and bone marrow (megakaryocytes). They therefore showed the TSP specificity known from the literature. However, surprisingly, there was also found to be a supernatant which reacted specifically with activated human platelets but not with the abovementioned normal tissues. The result was so surprising because there is no evidence in the cited literature suggesting an MAb specific for activated human platelets. The hybridoma cell which secreted this MAb was cloned 3×by the limited dilution technique and frozen in liquid nitrogen (hybridoma cell 2128). A detailed immunohistochemical analysis of specificity is shown in Table II. Beyond its high specificity for platelets, which was demonstrated using the APAAP technique (Cordell et al. supra), the MAb BW 2128 reacts >10×more strongly with thrombin-activated platelets than with non-activated platelets. Formaldehyde fixation of platelets only slightly inhibits the binding of the MAb to platelets. Addition of the MAb to non-activated human platelets leads to no significant activation, while addition of 0.5 units of thrombin/ml brings about extensive secretion of the activation marker (PF4) (Table III). MAbs specific for epitopes on granulocytes (for example BW 250) or on mycoplasmas (for example BW 227) and against GPIa/IIa (for example BW4) have, just like the MAb BW 2128, no effect on the activation of resting platelets (K. Boxxlet et al. European Journal of Nuclear Medicine (1988) 14, 523–528). The ELISA method for PF4 measurement after incubation of platelets under the conditions described in Table III is described by Pelzer, H., Heimburger, N. (1986), J. Biomed. Mat. Res. 20:1401–1409 and OseiBonsu, A., Cafourek, G., Reiter, S., Popovic, R., Sinzinger, H. (1987), Wiener klin. Wschr. 99:595–600. These properties distinguish the MAb BW 2128 from the anti-TSP MAbs generated by Dixit, V. M., Hayerstick, D. M., O'Rourke, K. M., Hennessy, S. W., Grant, G. A., Santoro, S. A., Frazier, W. A. (1985), Biochemistry 24:4270–4275, and from the anti-multimerin MAb JS-1 described by Hayward, C. P. M., Warkentin, T. E., Horsewood, P., Kelton, J. G. (1991), Blood 77:2556–2560, which influence the biological properties mentioned. It was possible by immunoprecipitation and Western blotting to show that the platelet antigen recognized by MAb BW 2128 is not identical to gP 140, v. Willebrand factor, fibronectin and fibrinogen.

Furthermore, using MAbs selective for 3 independent non cross-reactive epitopes on TSP (MAbs BW 2125/8, BW 2126/332, BW 2126/662; epitope mapping was performed according to Hammarström et al, Cancer Res. 49, 4852–4858, 1989), it could be shown that these MAbs strongly bind to purified TSP but not to the platelet antigen recognized by MAb BW 2128 as revealed in a standard solid phase ELISA system as well as by Western blotting analysis under non-reducing conditions. These experiments show that the platelet antigen defined by MAb BW 2128 does not share the 3 epitopes detected by the above mentioned anti TSPMAbs with TSP. In addition it was possible to show by 2D gel electrophoresis (O'Farrell, P. H. (1975), J. Biol. Chem. 250, 4007–4021) that the MAb precipitates an antigen which has under reducing conditions a molecular weight which is less than that of TSP and has a relative molecular mass of approximately 150,000 to 170,000, preferably of approximately 160,000, but has an isoelectric point like TSP which is not distinguishable within the limits of experimental error, preferably in the range of approximately 5.5–6.5

(TSP had a molecular weight of 180 KDa and an isoelectric point of 5.5 to 6.5 in a comparison experiment). This novel antigen is associated with TSP, with both physical and chemical binding being possible, and is preferentially expressed on activated platelets and is therefore generally designated as platelet antigen. The antigen also shows preferably the tissue distribution detailed in Table II.

The antigen, which can be isolated, for example, by immunoaffinity chromatography, preferably with the aid of the MAb BW 2128, is particularly suitable for preparing and checking antibodies equivalent to MAb BW 2128, or immunologically reactive parts thereof, and for preparing mimetics.

The antibodies according to the invention can be labeled with radioactive isotopes, especially with Tc-99m (Schwarz, A., Steinstraesser, A. (1987). J. Nucl. Med. BW 2128.Another possibility is the labeling with paramagnetic compounds. The antibodies and mimetics according to the invention are, accordingly, particularly suitable for the immunoscintigraphic visualization of vascular occlusions.

The hybridoma 2128 was deposited at the DSM, Deutsche Sammlung yon Mikroorganismen und Zellkulturen GmbH (Mascheroder Weg 1B, 3300 Braunschweig) in accordance with the Budapest Treaty under deposit number DSM ACC 2024. In addition, the V genes of the heavy and light chains of the MAb BW 2128 were isolated by the method described by Orlandi, R., Güssow, Do, Jones, P. T., Winter, G. (1989). Proc. Nat. Acad. Sci. USA 86:3833–837, and the nucleic acid sequence of the essential regions of the V gene exon was determined by the method described by Sanger, F., Nicklen, S., Coulson, A. R. (1977). Proc. Nat. Acad. Sci. USA 74:5463–5467 (Tab. Ia, (SEQ ID NO: 1 and 5). The cloned V genes were expressed as chimeric MAbs BW Chi 2128 with human truncated IgG3 Fc Part (IgG34) and human C kappa in BHK cells (Wirth, M., Bode, J., Zettlmeissl, G., Hauser, H. (1988). Gene 73:419–426) in order to confirm the identity of the cloned V genes (Examples A–N).

The expressed BW Chi 2128 MAbs showed the same antigen-binding specificity as the mouse MAb. It is furthermore possible, for example after polypeptide synthesis of the CDRs or of parts or several defined CDRs, for the mrus (minimal recognition units) to be determined and employed as specific peptides of low immunogenicity for the in vivo localisation of activated platelets. It is furthermore possible to generate by Organic chemical synthesis by the method described by Saragovi, H. U., Fitzpatrick, D., Raktabutr, A., Nakanishi, H., Kahn, M., Greene, M. I. (1991). Science 253:792–795 a mimetic with high specificity and avidity for the epitope defined by MAb BW 2128. The humanized V region of the MAb BW 2128 can be linked by recombination, for example, to nucleotide sequences which code for fibrinolytic proteins such as streptokinase, urokinase and tPA, but especially tPA mutants. Preferred tPA mutants can be prepared, for example, as described in EP-A1-0 387 380. These constructs can, as shown in German Patent Application P 41 06 389.9 by the example of a humanized eCEAMAb and of human β-glucuronidase, be linked at the level of the DNA and expressed as functional fusion proteins. In general, said fusion proteins represent, because of the combination of a specific high-affinity binding region for activated platelets in vascular occlusions and a functionally active region in the same molecule, efficient fibrinolytics with few side effects (Haber, E., Quertermous, Th., Matsueda, G. R., Runge, M. S., Bode, Ch. (1989). Jap. Circulation J. 54:345–353).

EXAMPLE A:

The plasmid clone 54.1.24, which harbors the human IgG$_3$ C gene (DE 3825615A1, FIG. 2) was cleaved with PstI. The vector resulting from this was ligated to the largest of the resulting PstI insert fragments and transformed into bacteria. The plasmid clone A which harbors a human IgG$_3$ C gene in which the H1, H2 and H3 exons are deleted (FIG. 2) was identified by restriction analysis and nucleic acid sequence determination.

Figure 3:
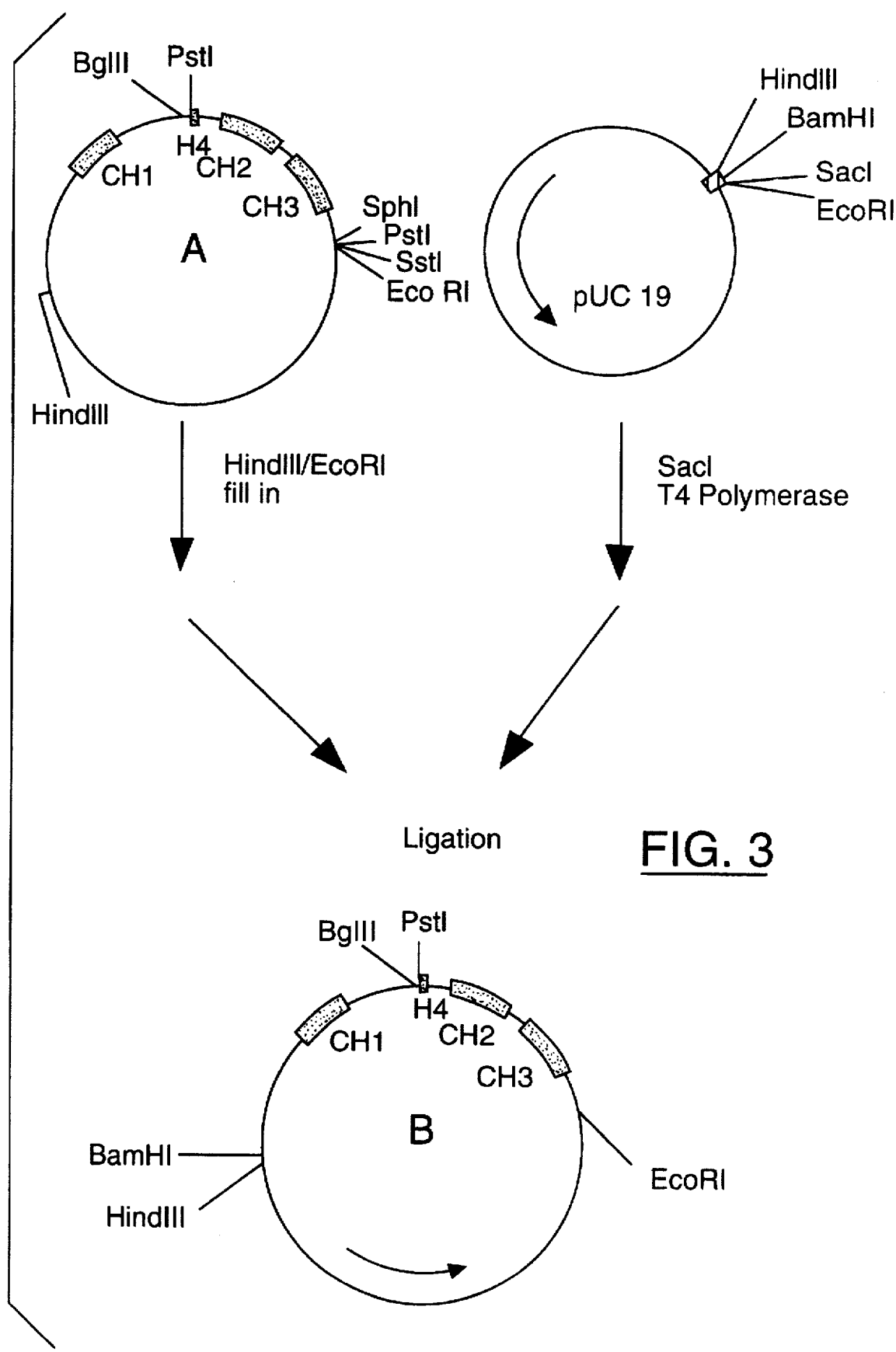

EXAMPLE B:

The plasmid clone A was cleaved with HindIII and EcoRI, the ends were filled in with Klenow polymerase, and the IgG$_3$ insert was isolated and ligated into a pUC19 vector which had been cleaved with SstI and provided with blunt ends with the aid of T$_4$ polymerase. A plasmid clone B in which the IgG$_3$ gene is oriented so that the HindIII cleavage site is located at the 5' end, and the EcoRI cleavage site is located at the 3' end of the pUC19 polylinker was identified by restriction mapping and nucleic acid sequence analysis (FIG. 3).

Figure 4:
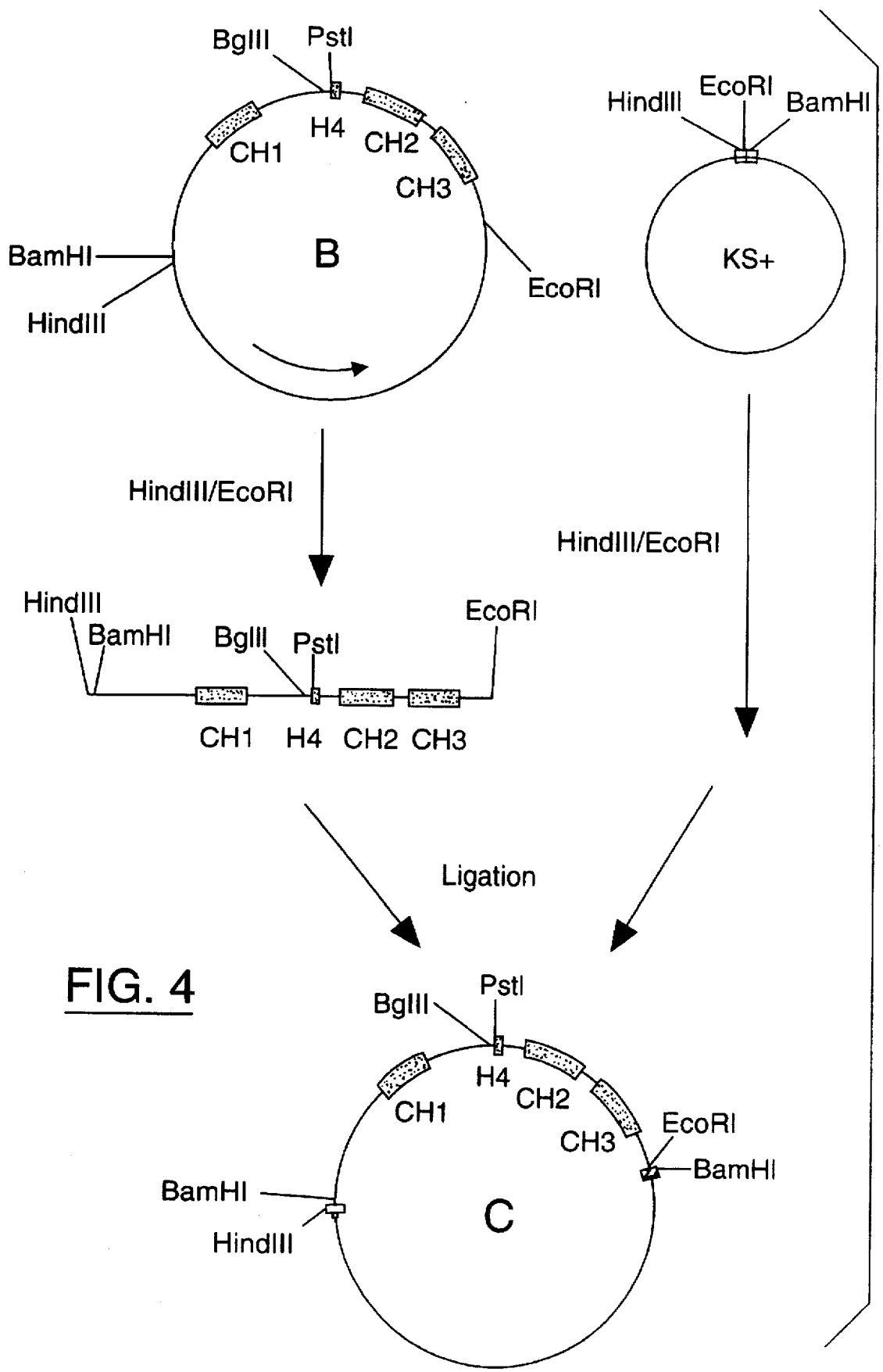

EXAMPLE C:

The plasmid clone B was cleaved with EcoRI and HindIII, and the IgG$_3$ insert was isolated and ligated into a KS+ phasmid vector (pBluescriptII KS+; Stratagene, La Jolla, CA) likewise cleaved with HindIII and EcoRI. The phasmid clone C in which the IgG$_3$ gene is flanked by a BamHI cleavage site at the 5' and 3' end was isolated (FIG. 4).

Figure 5:
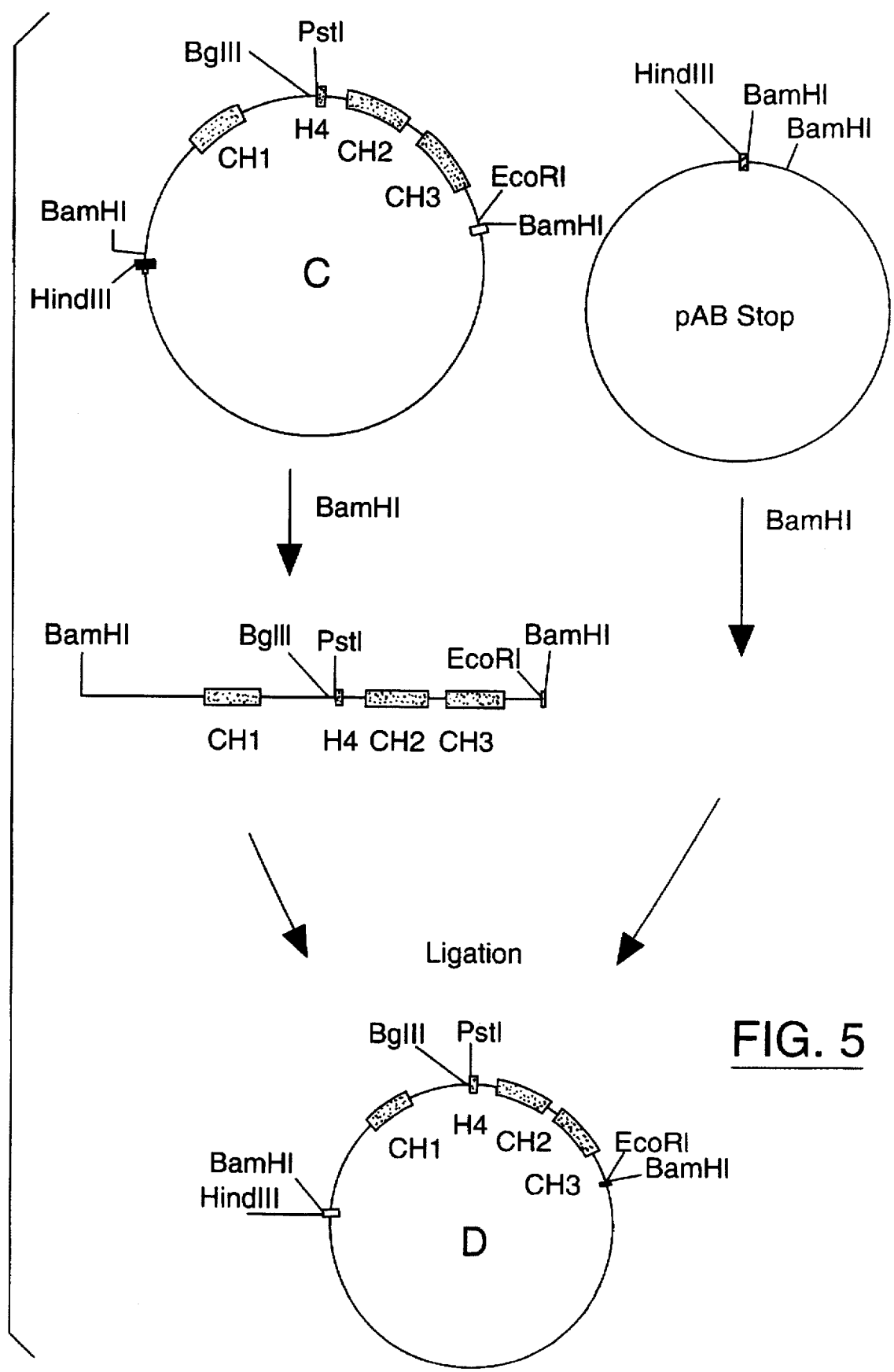

EXAMPLE D:

The phasmid clone C was cleaved with BamHI, and the IgG$_3$ insert was isolated and ligated into the expression vector pABStop (Wirth et al. supra) likewise cleaved with BamHI. The expression plasmid D which contains the IgG$_3$ C gene in the orientation shown in the formula was identified. In this cloning step the pABStop vector loses the SV40 stop and polyadenylation signal located between the two BamHI cleavage sites (FIG. 5).

EXAMPLE E:

The expression plasmid D was partially cleaved with BamHI, and the ends were filled in with Klenow polymerase and religated. The expression plasmid E in which the BamHI cleavage site 3' from the IgG$_3$ gene is destroyed was isolated (FIG. 6).

Figure 7:
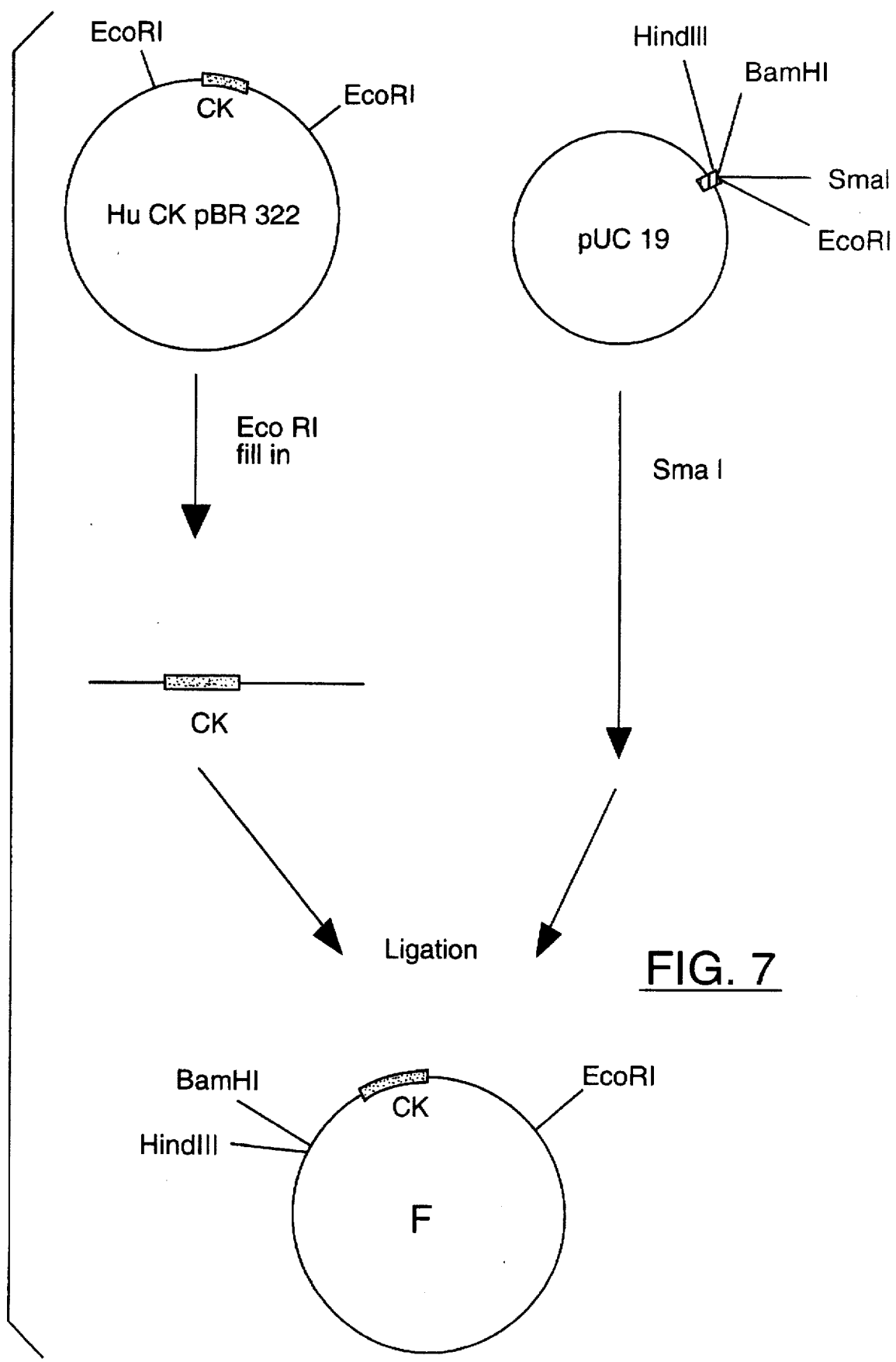

EXAMPLE F:

The human C kappa gene (Hieter, P. A., Mainzel, J. V., Jr., Leder, P. (1982), The Journal of Biological Chemistry, 257:1516–1522) was cloned as EcoRI fragment into pBR 322. The pBR322 vector was cleaved with EcoRI, the EcoRI cleavage sites were filled in, and the C kappa insert was isolated and ligated into a pUC19 vector cleaved with SmaI. The plasmid clone F in which the C kappa gene is flanked by a HindIII and a BamHI cleavage site at the 5' end, and by an EcoRI cleavage site at the 3' end was isolated (FIG. 7).

Figure 8:
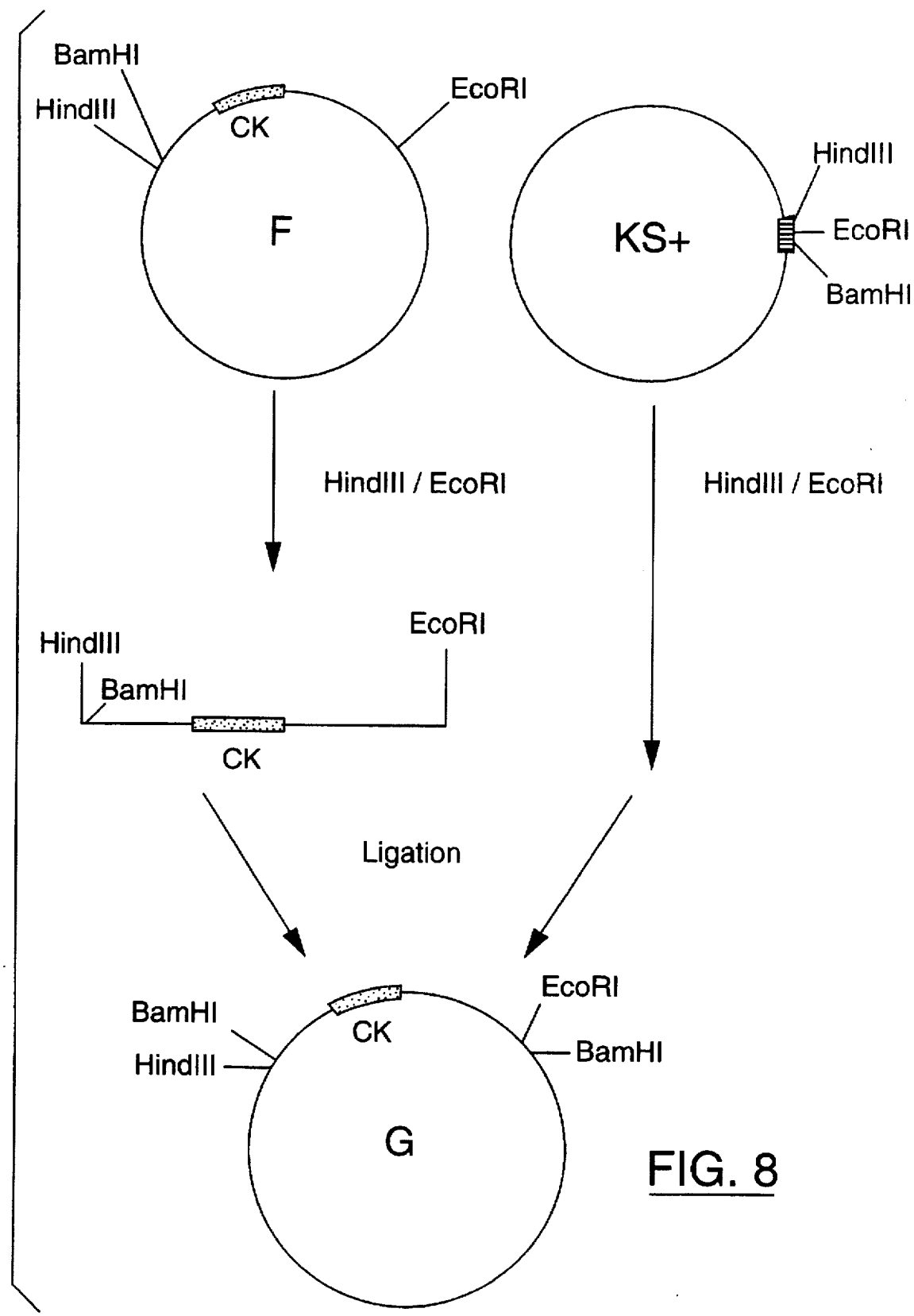

EXAMPLE G:

The plasmid clone F was cleaved with HindIII and EcoRI, and the C kappa insert was isolated and cloned into a KS+ phasmid cleaved with HindIII/EcoRI. The phasmid clone G in which the C kappa insert is flanked by a BaEHI cleavage site at the 5' and at the 3' end was isolated (FIG. 8).

Figure 9:
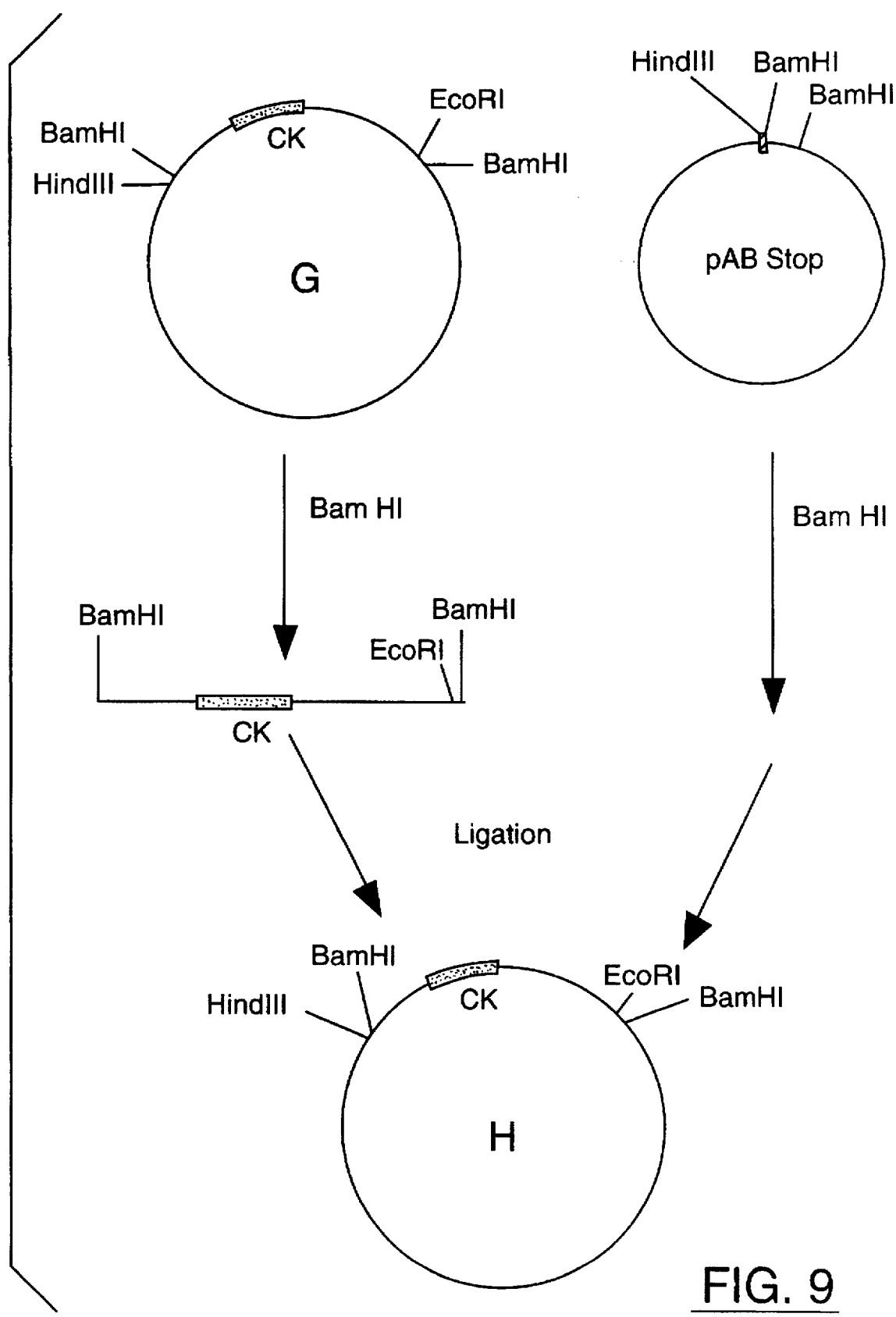

EXAMPLE H:

The phasmid clone G was cleaved with BamHI, and the C kappa insert was isolated and cloned into a pAB stop vector cleaved with BamHI. The clone H in which the C kappa gene is oriented so that the HindIII cleavage site of the pAB stop vector is located at its 5' end was identified by restriction mapping and nucleic acid sequence analysis (FIG. 9).

Figure 10:
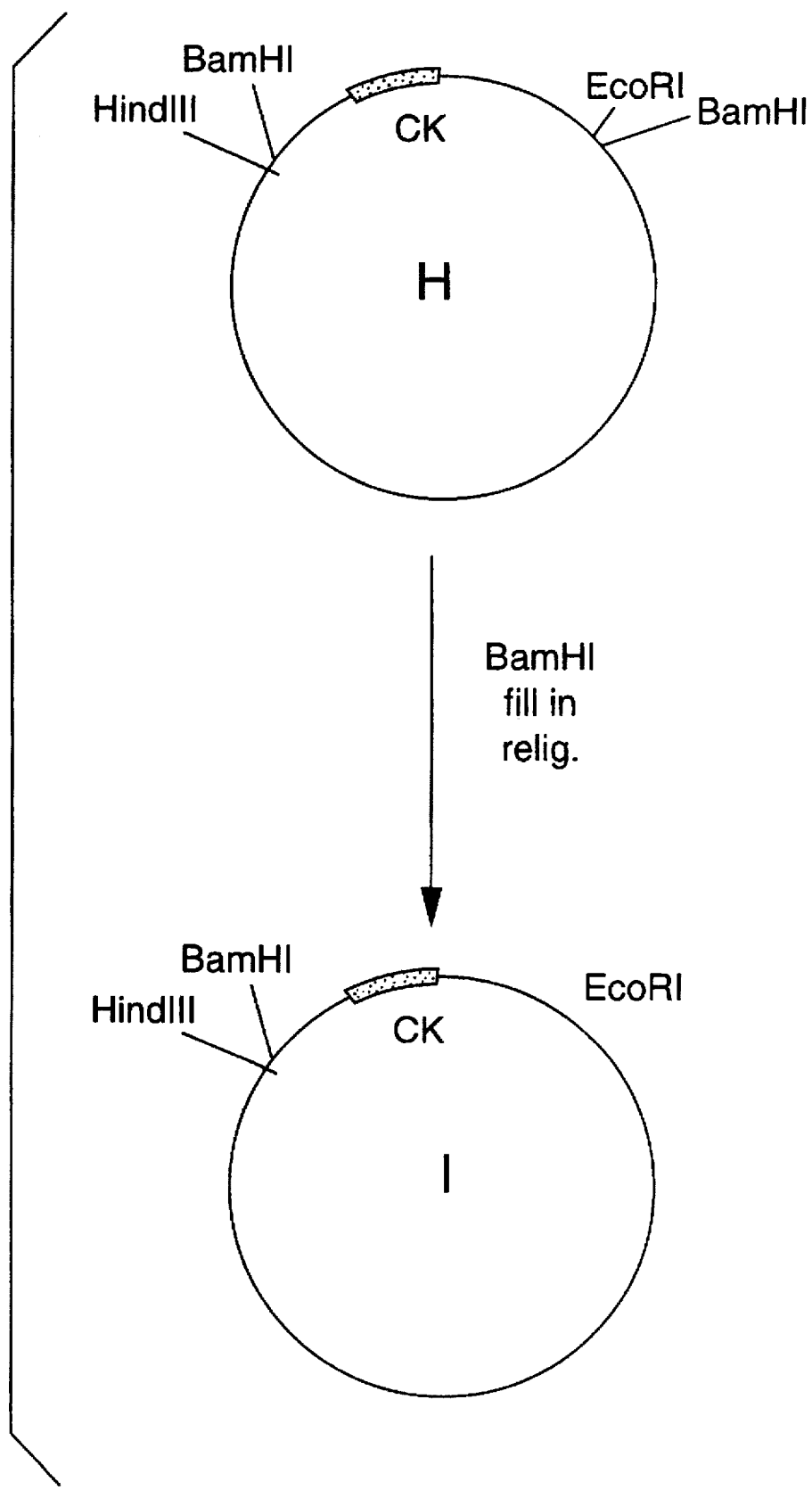

EXAMPLE I:

The clone H was partially cleaved with BamHI, and the restriction ends were filled in and religated. The clone I in which the BamHI cleavage site 3' of the C kappa gene is destroyed was identified by restriction mapping (FIG. 10).

Figure 11:
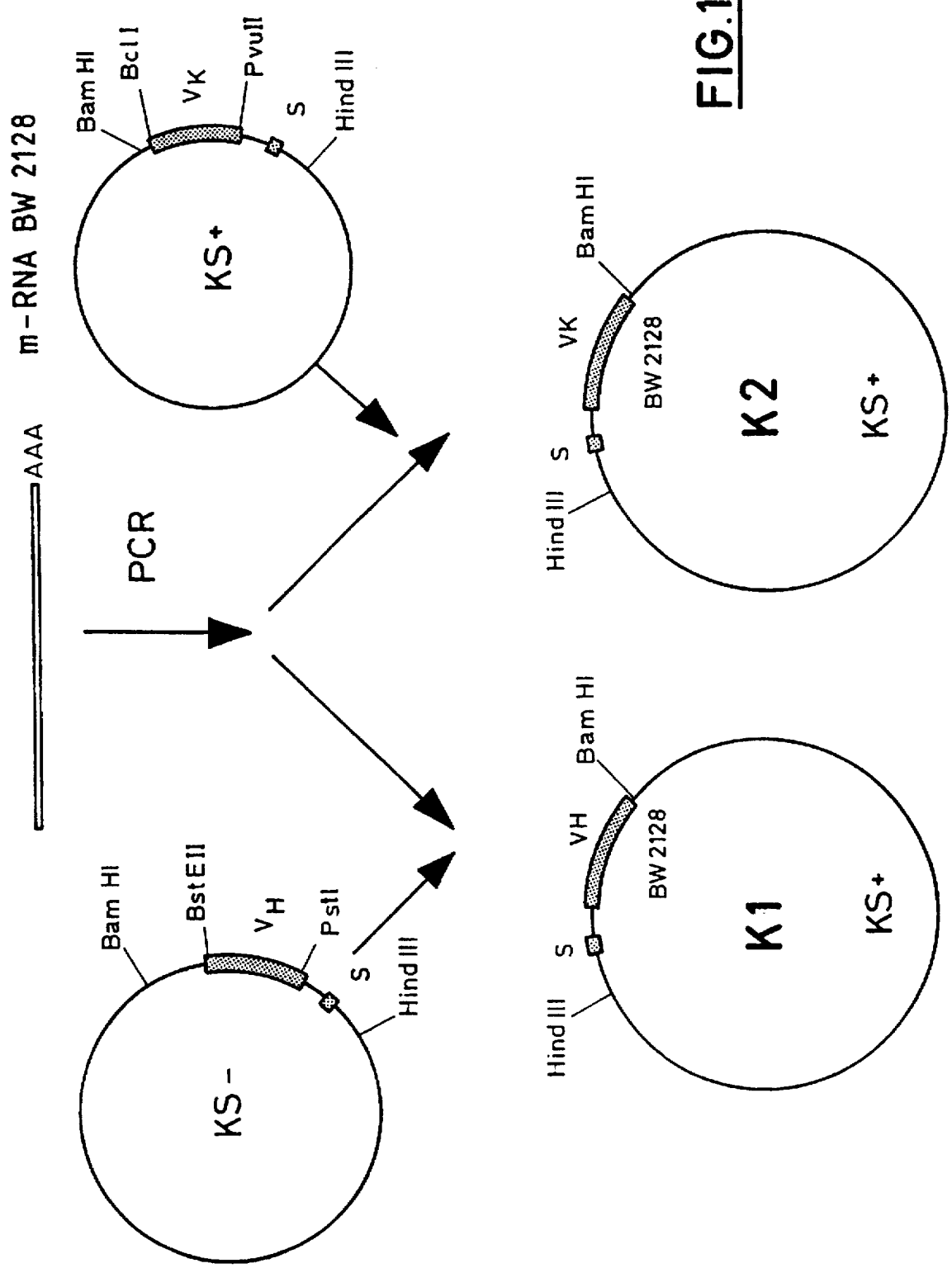
Figure 12:
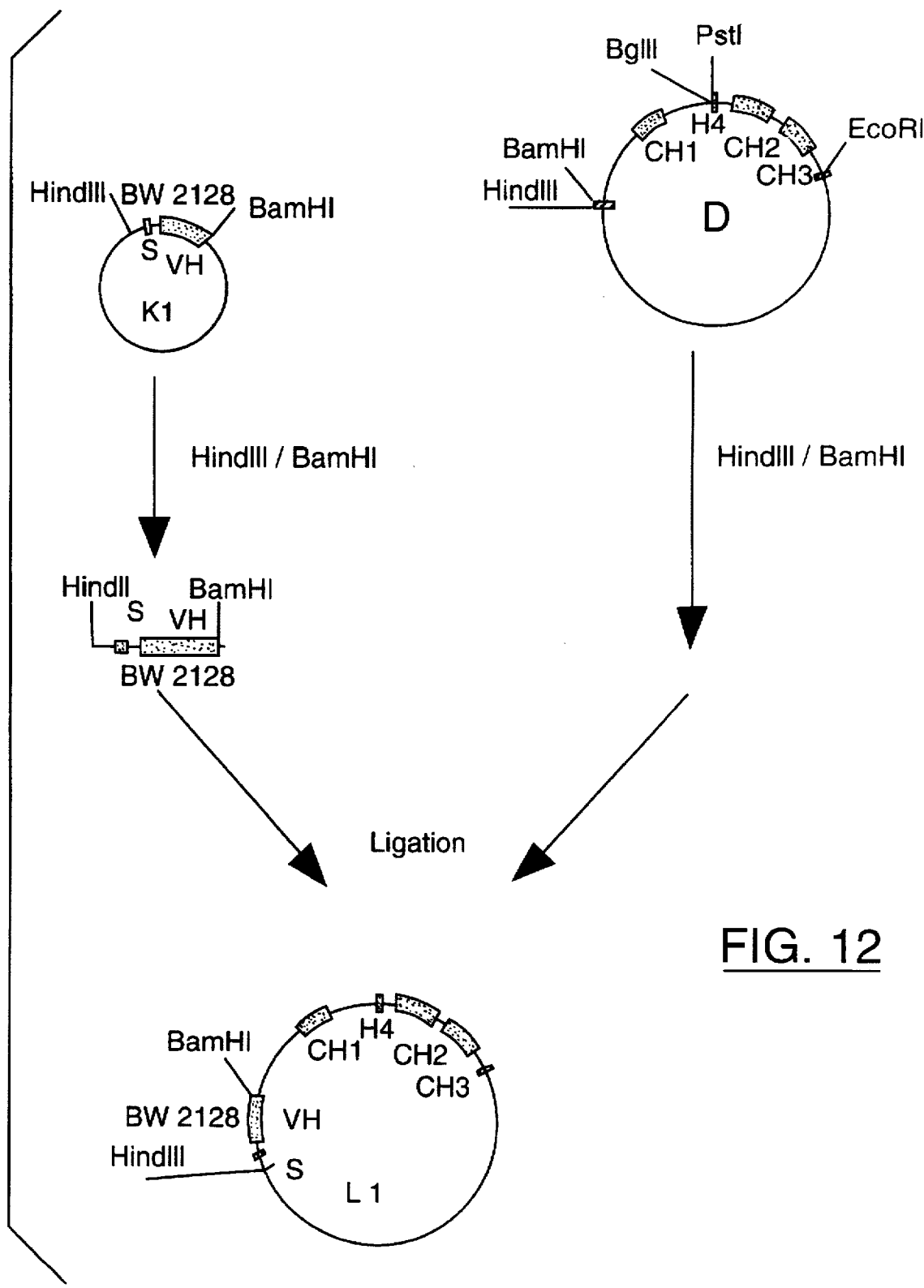
Figure 13:
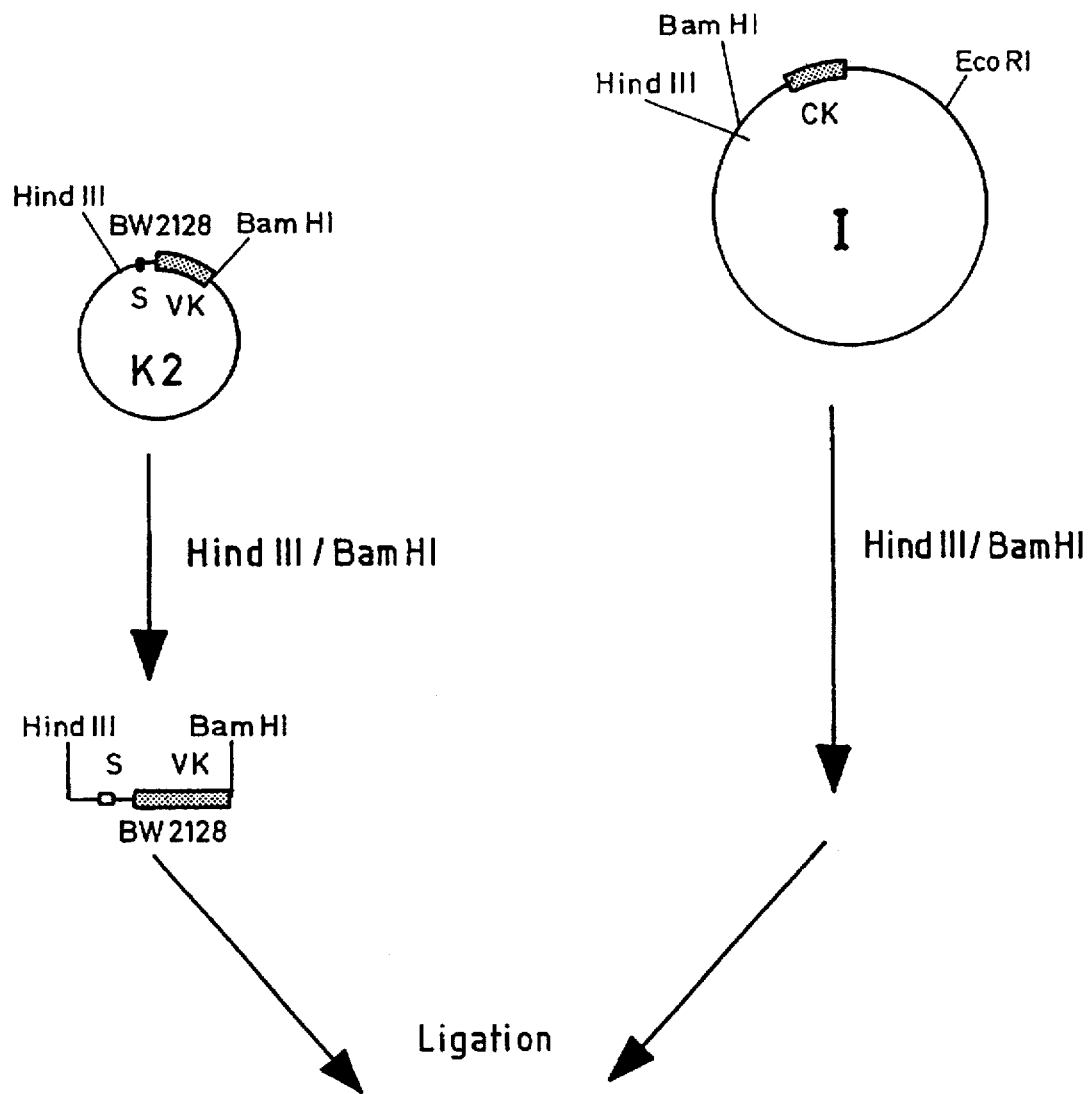
Figure 13:
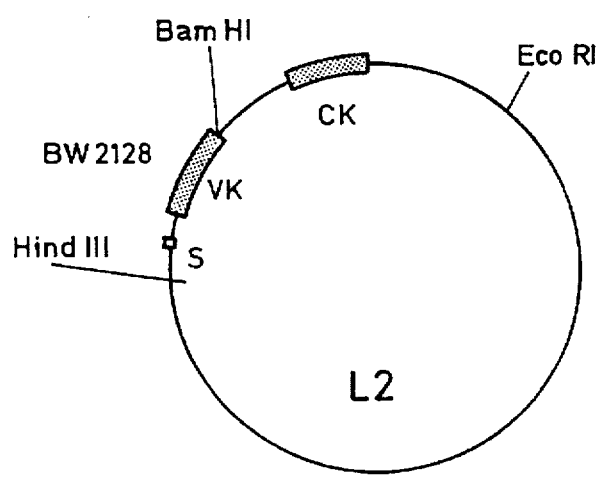
Figure 14:
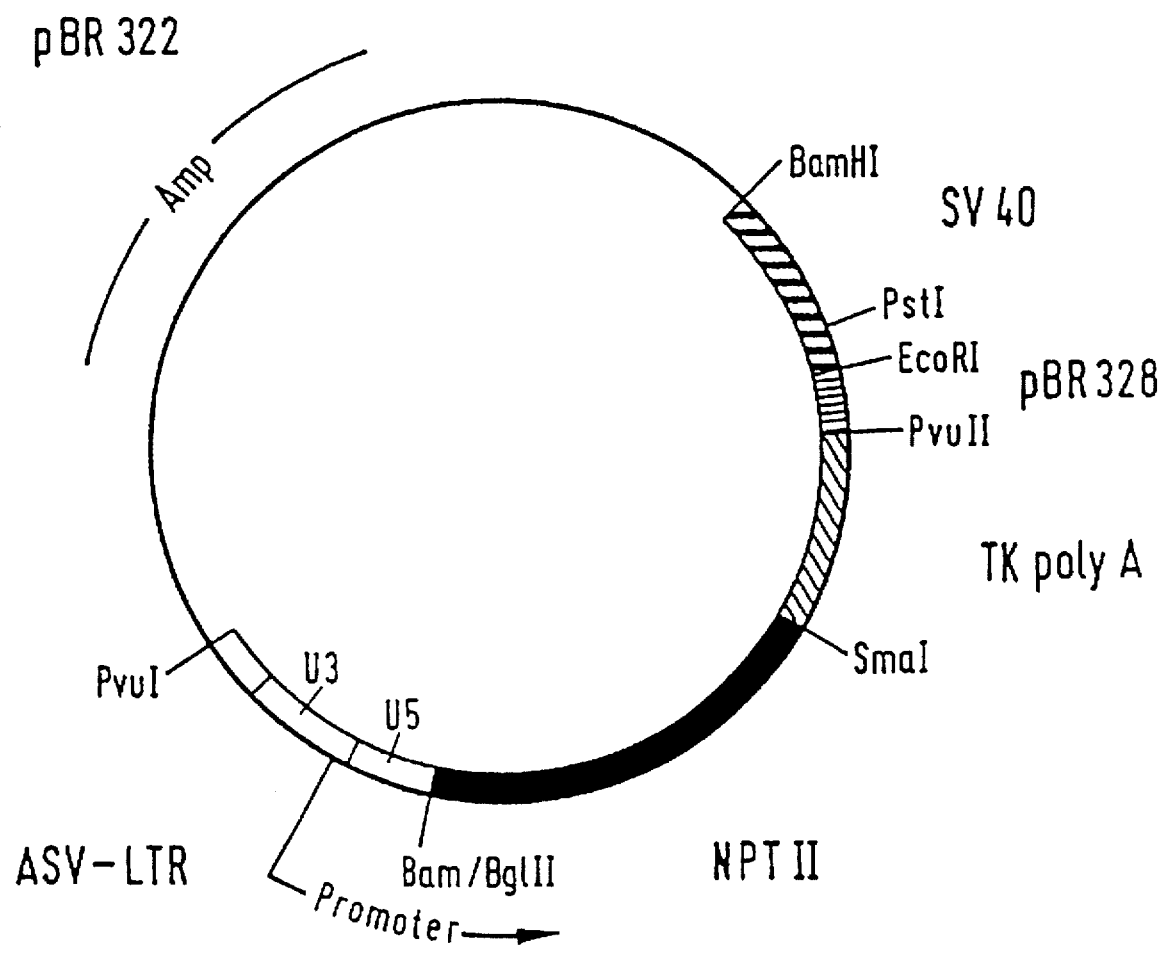
Figure 15:
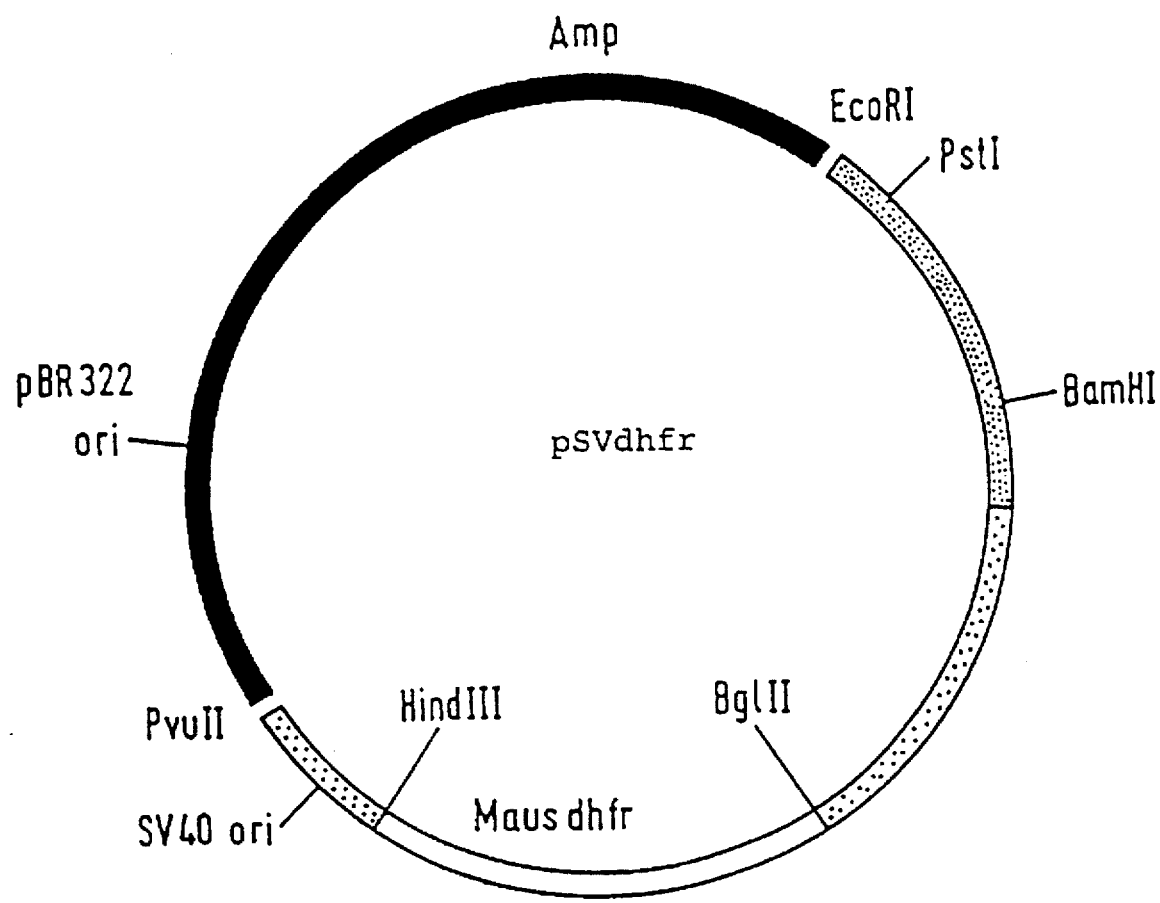

EXAMPLE K:

The $V_H$ and $V_K$ genes of MAb BW 2128 were amplified as described by Orlandi et al. (supra) using the PCR technique and specific oligonucleotides and cloned into KS+ vectors (Güssow, D. and Seemann, G. (1992). Methods in Enzymology, Vol. 203, 99–121), which contained irrelevant $V_H$ and $V_K$ genes with suitable restriction cleavage sites. The clones K1 and K2 in which the irrelevant $V_H$ and $V_L$ genes have been replaced by the $V_H$ (K1) and $V_K$ (K2) genes of MAb BW 2128 were subsequently isolated (FIG. 11).

EXAMPLE L:

The nucleic acid sequence of the $V_H$ and $V_K$ genes of MAb BW 2128 was determined by the method of Sanger PNAS, 74, 463 (1977) from the clones K1 and K2 (Tab. Ia, b).

EXAMPLE M:

The $V_H$ and $V_K$ genes of MAb BW 2128 were cut out of the clones K1 and K2 with the aid of the restriction enzymes HindIII and BamHI, and the V gene inserts were isolated and cloned into the expression vectors $D(V_H)$ and $I(V_K)$ cut with HindIII and BamHI. The expression vectors L1 (FIG. 12) and L2 (FIG. 13) which contain a complete immunoglobulin heavy chain gene (L1) or light chain gene (L2) were isolated.

EXAMPLE N:

The expression vectors L1 and L2 were transfected together with the vector pR11 H140 (Hudziak, R. M., Laski, F. A., RajBhandary, U. L., Sharp, P. A., Capecchi, M. R. (1982), Cell 31:137–146) which confers neomycin resistance (FIG. 14) and with the vector pSVdhfr (Lee, F., Mulligan, R., Berg, P., Ringold, G. (1981), Nature 294:228–232) which carries a dihydrofolate reductase gene and confers resistance to methotrexate (FIG. 15) into BHK cells (ZettlmeiBl, G., Wirth, M., Hauser, H., Küpper, H. A. (1988). Behring Inst. Mitt. 82:26–34), and the expressed antibody was investigated for antigen-binding properties in order to confirm the identity of the $V_H$ and $V_K$ genes of MAb BW 2128.

EXAMPLE O:

The immunohistochemical analysis of the specificity of the antibodies according to the invention was carried out by the APAAP technique (Cordell et al., supra). Table II shows the result of an immunohistochemical analysis of the specificity of MAb BW 2128.

EXAMPLE P:

The platelet activation can be measured by quantitative determination of the activation marker PF4 with the aid of the ELISA described by H. Pelzer and N. Heimburger (supra). Table III shows the effect of MAb BW 2128 on platelet activation.

Tab. Ia

2128 VH Mouse

```
1
CTG CAG CAG TCT GGG GCT GAA CTG GTG AAG CCT GGG GCT TCA GTG ACC CTG TCC TGT AAG
leu gln gln ser gly ala glu leu val lys pro gly ala ser val thr leu ser cys lys
61
GCT TCT GGC TAC ACC TTC ACC AGC TAC TGG ATG CAC TGG GTG AAG CAG AGG CCT GGA CAA
ala ser gly tyr thr phe thr ser tyr trp met his trp val lys gln arg pro gly gln
121
GGC CTT GAG TGG ATT GGA GAG ATT AAT CCT AGC AAC GGT CGT ACT AAC TAC AAT GAG AAG
gly leu glu trp ile gly glu ile asn pro ser asn gly arg thr asn tyr asn glu lys
181
TTC AAG AGC AAG GCC ACA CTG ACT GTA GAC AAA TCC TCC AGC ACA GCC TAC ATG CAC CTC
phe lys ser lys ala thr leu thr val asp lys ser ser ser thr ala tyr met his leu
241
AGC AGC CTG ACA TCT GAT GAC TCT GCG GTC TAT TAC TGT GCA AGA GGG GCT GGG GCG GGA
ser ser leu thr ser asp asp ser ala val tyr tyr cys ala arg gly ala gly ala gly
301
GGC TAC TGG GGC CAA GGG ACC ACG GTC ACC GTC TCC TCA GGT GAG TCC TTA CAA CCT
gly tyr trp gly gln gly thr thr val thr val ser ser gly glu ser leu gln pro
```

VH gene family IIB

Tab. Ib

2128 VK Mouse

```
1
CAG CTG ACC CAG TCT CCA GCA ATC ATG TCT GCA TCT CCA GGG GAG AAG GTC ACC ATG ACC
gln leu thr gln ser pro ala ile met ser ala ser pro gly glu lys val thr met thr
61
TGC AGT GCC AGC TCA AGT GTA ACT TAC ATG CAC TGG TGC CAG CAG AAG TCA GGC ACC TCC
cys ser ala ser ser ser val thr tyr met his trp cys gln gln lys ser gly thr ser
121
CCC AAA AGA TGG ATT TAT GAC ACA TCC AAA CTG GCT TCT GGA GTC CCT GCT CGC TTC AGT
pro lys arg trp ile tyr asp thr ser lys leu ala ser gly val pro ala arg phe ser
181
GGC AGT GGG TCT GGG ACC TCT TAC TCT CTC ACA ATC AGC AGC ATG GAG GCT GAA GAT GCT
gly ser gly ser gly thr ser tyr ser leu thr ile ser ser met glu ala glu asp ala
241
GCC ACC TAT TAC TGC CAG CAG TGG AAT AGT AAC CCG CTC ACG TTC GGT GCT GGG ACC AAG
ala thr tyr tyr cys gln gln trp asn ser asn pro leu thr phe gly ala gly thr lys
```

Tab. Ib-continued

```
301
CTG GAG ATC
leu glu ile
```

VK gene family VI

TABLE II

Immunohistochemical analysis of the specificity of the MAb

| Tissues | Tested | Reaction type pos. | neg. |
|---|---|---|---|
| Platelet pellet | 12 | +++ | |
| Granulocyte pellet | 10 | – | |
| Mono/lymphocyte pellet | 10 | +/++ | |
| Normal tissue | | | |
| Lymph nodes | 2 | – | Bgfas – |
| Heart | 2 | – | Bgfas – |
| Pericardium | 4 | eThrom+/++ | Bgfas – |
| Nerves | 1 | – | Nervenfas – |
| Tonsils | 1 | – | Fas – |
| Spleen | 4 | Throm++/+++ | Gef –, Fas – |
| Gastric mucosa | 1 | – | Gef –, Fas – |
| Intestinal mucosa | 1 | ewThrom+ | Gef –, Fas – |
| Muscle | 5 | eSark,Fib+ | |
| Putamen | 1 | – | Fas – |
| Liver | 5 | eThrom++ | G–,Gef–,Fas– |
| Lung | 4 | ewThrom+ | Gef–,Pneumo– |
| Bone marrow | 4 | ewThrom+ | Megakaryo.– |
| Kidney | 3 | ewThrom+ | Gef –, Kan – |
| Human Carcinomas | | | |
| Gastric carcinoma | 2 | ewThrom+ | Gef–, Bgfas– |
| Pancreas carcinoma | 2 | ewThrom+ | Gef – |
| Bronchial carc.-adeno | 1 | – | Gef – |
| -small cell | 1 | – | Gef – |
| -squamous cell | 1 | – | Gef – |

TABLE II-continued

Immunohistochemical analysis of the specificity of the MAb

| Tissues | Tested | Reaction type pos. | neg. |
|---|---|---|---|
| Breast carcinoma | 2 | – | Gef – |
| Glioblastoma | 2 | ewThrom+ | Gef – |
| Melanoma | 2 | ewThrom+ | Gef – |
| Colon carcinoma | 1 | – | Gef–, Bgfas– |
| Rectum carcinoma | 1 | – | Gef – |

Key:

ewThrom - few platelets eThrom - some platelets

G - ducts

Gef - vessels

Kan - tubules

Bgfas - connective tissue fibe

Fas - fibers

Pneumo - pneumocytes, type II

Sark - sarcolemma

Fib - fibrils

Megakaryo - megakaryocytes

TABLE III

Effect of Mab BW 2128 on platelet activation

| Platelet preparation: | Release of PF4 in µg/ml after incubation with 20 µg at 37° C. for 30' | | | | |
|---|---|---|---|---|---|
| | MAb BW 2128 | MAb BW 250 | MAb BW 4 | BW 227 | Thrombin (0.5 U/ml) |
| Platelet-rich plasma | 45 | 60 | 132 | 94 | 2000 |
| Washed platelets | 110 | 178 | 181 | 142 | 1900 |
| Thrombin-activated platelets | 1800 | 1600 | 1500 | 1400 | |

We claim:

1. The hybridoma 2128 (DSM ACC2024).

2. A monoclonal antibody which is obtained from the hybridoma 2128 (DSM ACC2024).

3. Monoclonal antibodies or antigen binding fragments thereof which bind to an epitope which is recognized by a monoclonal antibody as claimed in claim 2.

4. Monoclonal antibodies or antigen binding fragments thereof which preferentially bind to activated human platelets and having the amino-acid sequence as shown in Tab. Ia (SEQ IN NO: 2).

5. A monoclonal antibody or antigen binding fragments thereof as claimed in claim 3, wherein the antibody is a chimeric, humanized, bi- or oligospecific antibody.

6. A monoclonal antibody as claimed in claim 3, wherein the antibody is an mru fragment, a single domain fragment, a single chain fragment, an F(ab) fragment or an F(ab')$_2$ fragment with one or more hinge regions.

7. Monoclonal antibodies as claimed in claim 5, wherein the chimeric antibody is BW Chi 2128.

8. A monoclonal antibody as claimed in claim 2, which is labeled, preferably with Tc-99m.

9. A mimetic which binds to an epitope which is recognized by a monoclonal antibody as claimed in claim 2.

10. A polypeptide containing an amino-acid sequence as shown in Tab. Ia (SEQ ID NO: 2) and/or Tab. Ib (SEQ IN NO: 4) which specifically binds to the epitope which is recognized by a monoclonal antibody as claimed in claim 2.

11. A pharmaceutical composition containing a monoclonal antibody as claimed in claim 2.

12. A pharmaceutical composition containing polypeptides as claimed in claim 10.

13. A diagnostic aid containing a monoclonal antibody as claimed in claim 2.

14. A diagnostic aid containing polypeptides as claimed in claim 10.

15. A method for preparing a diagnostic aid for the detection of activated human platelets comprising incorporating the monoclonal antibody as claimed in claim 2 into a diagnostic aid.

16. A method for preparing a diagnostic aid for the detection of activated platelets comprising incorporating the polypeptide as claimed in claim 10 into a diagnostic aid.

* * * * *

UNITED STATES PATENT AND TRADEMARK OFFICE
CERTIFICATE OF CORRECTION

PATENT NO. : 5,686,583
DATED : November 11, 1997
INVENTOR(S) : Klaus BOSSLET et al.

It is certified that error appears in the above-identified patent and that said Letters Patent is hereby corrected as shown below:

Claim 4, column 13, line 44, "IN" should read --ID--;
and after "NO: 2)", insert --and/or Tab.Ib (SEQ ID NO:4)--.

Claim 10, column 14, line 37, "IN" should read --ID--.

Signed and Sealed this

Eleventh Day of August 1998

Attest:

BRUCE LEHMAN

*Attesting Officer*    *Commissioner of Patents and Trademarks*